US007899522B1

(12) United States Patent
Koh et al.

(10) Patent No.: US 7,899,522 B1
(45) Date of Patent: Mar. 1, 2011

(54) SYSTEM AND METHOD FOR DISCRIMINATING ACUTE AND CHRONIC HEART FAILURE USING AN IMPLANTABLE MEDICAL DEVICE

(75) Inventors: Steve Koh, South Pasadena, CA (US); Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 832 days.

(21) Appl. No.: 11/549,569

(22) Filed: Oct. 13, 2006

(51) Int. Cl.
*A61B 5/04* (2006.01)
(52) U.S. Cl. .................. 600/513; 600/508; 600/547
(58) Field of Classification Search ............. 600/508, 600/513, 516, 517, 547; 607/18
See application file for complete search history.

(56) References Cited

U.S. PATENT DOCUMENTS

| | | | |
|---|---|---|---|
| 4,759,366 A | 7/1988 | Callaghan | |
| 5,328,460 A | 7/1994 | Lord et al. | |
| 5,476,483 A | 12/1995 | Bornzin et al. | |
| 5,817,135 A | 10/1998 | Cooper et al. | |
| 5,861,008 A | 1/1999 | Obel et al. | |
| 5,876,353 A | 3/1999 | Riff | |
| 5,957,861 A * | 9/1999 | Combs et al. ............... 600/547 |
| 6,002,963 A | 12/1999 | Mouchawar et al. | |
| 6,128,534 A | 10/2000 | Park et al. | |
| 6,129,744 A * | 10/2000 | Boute ........................... 607/25 |
| 6,249,705 B1 | 6/2001 | Snell | |
| 6,336,903 B1 * | 1/2002 | Bardy ......................... 600/508 |
| 6,473,640 B1 | 10/2002 | Erlebacher | |
| 6,480,733 B1 | 11/2002 | Turcott | |
| 6,512,949 B1 | 1/2003 | Combs et al. | |
| 6,512,952 B2 | 1/2003 | Stahmann et al. | |
| 6,512,953 B2 | 1/2003 | Florio et al. | |
| 6,527,729 B1 | 3/2003 | Turcott | |
| 6,572,557 B2 | 6/2003 | Tchou et al. | |
| 6,595,927 B2 | 7/2003 | Pitts-Crick et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,741,885 B1 | 5/2004 | Park et al. | |
| 6,748,261 B1 | 6/2004 | Kroll et al. | |
| 6,829,503 B2 | 12/2004 | Alt | |
| 6,922,587 B2 | 7/2005 | Weinberg | |
| 6,942,622 B1 | 9/2005 | Turcott | |
| 7,069,069 B2 | 6/2006 | Fishler et al. | |
| 7,096,061 B2 * | 8/2006 | Arad ............................ 600/547 |
| 2004/0102712 A1 | 5/2004 | Belalcazar et al. | |

* cited by examiner

*Primary Examiner*—Carl H Layno
*Assistant Examiner*—Pamela M Bays

(57) ABSTRACT

Techniques are provided for evaluating heart failure within a patient. In one example, the implantable device detects a decrease, if any, in selected morphological parameters derived from the intracardiac electrogram (IEGM) that are indicative of possible heart failure, such as paced depolarization integrals (PDI) or peak-to-peak amplitudes of QRS-complexes. The device also detects a decrease, if any, in transthoracic impedance, which is also indicative of possible heart failure. Acute heart failure is indicated if there is a decrease in the morphological IEGM parameters but no significant decrease in transthoracic impedance. Chronic heart failure is indicated if there is a decrease in transthoracic impedance but no significant decrease in the morphological IEGM parameters. If both transthoracic impedance and the morphological IEGM parameters are found to be decreasing significantly, the device issues a warning of severe heart failure.

17 Claims, 7 Drawing Sheets

SYSTEM AND METHOD FOR DISCRIMINATING ACUTE AND CHRONIC HEART FAILURE USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for detecting and evaluating heart failure within a patient in which a medical device is implanted.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

Pulmonary edema is a swelling and/or fluid accumulation in the lungs often caused by heart failure (i.e. the edema represents one of the "congestives" of CHF.) Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. This can cause severe respiratory problems and, left untreated, can be fatal. Pulmonary edema is usually associated with relatively severe forms of heart failure and is often asymptomatic until the edema itself becomes severe, i.e. the patient is unaware of the pulmonary edema until it has progressed to a near fatal state when respiration suddenly becomes quite difficult.

In view of the potential severity of heart failure/pulmonary edema, it is highly desirable to detect the onset of these conditions within a patient and to track the progression thereof so that appropriate therapy can be provided. Many patients suffering heart failure/pulmonary edema already have pacemakers or ICDs implanted therein or are candidates for such devices. Accordingly, it is desirable to provide such devices with the capability to automatically detect and track heart failure/pulmonary edema.

Heretofore, a number of techniques have been developed for detecting heart failure and/or pulmonary edema using implantable cardiac devices based on analysis of a transthoracic impedance signal. In this regard, the presence of additional fluids in the lungs tends to lower the electrical impedance measured between electrodes implanted in the heart and the housing of the implanted device. Hence, a sustained decrease in transthoracic impedance is indicative of possible pulmonary edema/heart failure. See, for example, U.S. patent application Ser. No. 11/138,229, of Koh et al., filed May 25, 2005, entitled "System and Method for Impedance-Based Detection of Pulmonary Edema and Reduced Respiration Using an Implantable Medical System." See, also, U.S. Pat. No. 5,876,353 to Riff, entitled "Impedance Monitor for Discerning Edema through Evaluation of Respiratory Rate"; U.S. Pat. No. 5,957,861 to Combs et al., entitled "Impedance Monitor for Discerning Edema through Evaluation of Respiratory Rate"; U.S. Pat. No. 6,512,949 also to Combs et al., entitled "Implantable Medical Device for Measuring Time Varying Physiologic Conditions Especially Edema and for Responding Thereto"; U.S. Pat. No. 6,473,640 to Erlebacher, entitled "Implantable Medical Device for Measuring Time Varying Physiologic Conditions Especially Edema and for Responding Thereto"; U.S. Pat. No. 6,595,927 to Pitts-Crick et al., entitled "Method and System for Diagnosing and Administering Therapy of Pulmonary Congestion"; U.S. Pat. No. 6,829,503 to Alt, entitled "Congestive Heart Failure Monitor"; and U.S. Patent Application 2004/0102712 of Belalcazar et al., entitled "Impedance Monitoring for Detecting Pulmonary Edema and Thoracic Congestion."

It is also feasible to detect heart failure based on analysis of morphological features of the intracardiac electrogram (IEGM). The IEGM is a voltage signal measured using electrodes implanted within the heart that corresponds to cardiac electrical activity associated with the contraction of the various chambers of the heart. It has been found that a paced depolarization integral (PDI) derived from the IEGM generally decreases due to heart failure, apparently due to changes in the contractility and thickness of the heart wall caused by heart failure. (PDI is a well-known parameter derived from an integral of portions of the IEGM. For a description of PDI, also sometimes referred to as a depolarization gradient, see U.S. Pat. No. 4,759,366, to Callaghan.) It has also been found that the peak-to-peak amplitude of the QRS-complex of the IEGM tends to decrease due to heart failure. The QRS complex is an electrical signal associated with ventricular depolarization. Further, it is know that the maximum slope of the QRS-complex (referred to as Δmax or Dmax) tends to decrease due to heart failure.

Hence, it is feasible to configure a pacemaker to detect and analyze changes in IEGM morphology as well as changes in transthoracic impedance and generate an indication of possible heart failure and/or pulmonary edema. However, the present inventors have recognized that the effect of heart failure on IEGM morphology and transthoracic impedance depends, at least in part, on the type and severity of the heart failure, particularly whether heart failure is acute or chronic. Accordingly, it would be desirable to provide techniques for discriminating acute and chronic heart failure from one another and for generating appropriate warning signals and controlling therapy in response thereto. It is also desirable to warn of possible pulmonary edema. The present invention is generally directed to these ends.

SUMMARY

In one embodiment, a method is provided for evaluating heart failure within a patient using an implantable medical device. Briefly, the device detects changes, if any, in cardiac electrical signals indicative of heart failure within the patient. The device also detects changes, if any, in transthoracic impedance indicative of heart failure within the patient. Then, the device distinguishes between acute and chronic heart failure within the patient based on the detected changes, if any, in the cardiac electrical signals and transthoracic impedance.

In an illustrative example, where the device is a pacemaker or ICD, the device detects a decrease, if any, in selected morphological parameters derived from the IEGM over the last thirty days including one or more of ventricular PDI, peak-to-peak amplitudes of QRS-complexes, and Dmax, any of which is indicative of possible heart failure. The device also detects a decrease, if any, in impedance (Z) measured over the last thirty days between the right ventricular (RV) tip electrode to the device case, which is indicative of possible pulmonary edema secondary to heart failure. The device then generates an indication of acute heart failure, if heart failure is indicated by the cardiac signals but not by the impedance values. The device generates an indication of chronic heart failure, if heart failure is indicated by the impedance values but not by the cardiac signals. In this manner, the device discriminates between acute and chronic heart failure.

In this regard, the inventors have recognized that IEGM morphology does not change significantly over the short term within patients suffering from chronic heart failure, most likely because changes in heart wall thickness and contractility caused by heart failure (which affect IEGM morphology) have already occurred. The inventors have also recognized that transthoracic impedance does not change significantly over the short term in patients suffering from acute heart failure, as acute heart failure has not yet had a chance to trigger an increase in pulmonary congestives. However, if both IEGM morphology and transthoracic impedance change significantly over the short term, such is an indication of severe heart failure. Accordingly, the device generates appropriate warning signals. Preferably, the warning signals are provided both to the patients (via implanted warning devices and/or bedside warning devices) and also to the appropriate physician/clinician (via a communication network connected to the bedside monitor) so that immediate corrective action can be taken. Also, once heart failure has been detected and evaluated, appropriate therapy can be automatically provided by the implanted device, which may include CRT (if the device is a bi-ventricular pacer) or drug therapy (if an implantable drug pump is provided with medication appropriate for heart failure and/or pulmonary edema.) Diagnostic information representative of the type and severity of heart failure as well as the presence of pulmonary congestives is also generated for review by the clinician/physician.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of the Heart Failure Discrimination System

Figure 1:
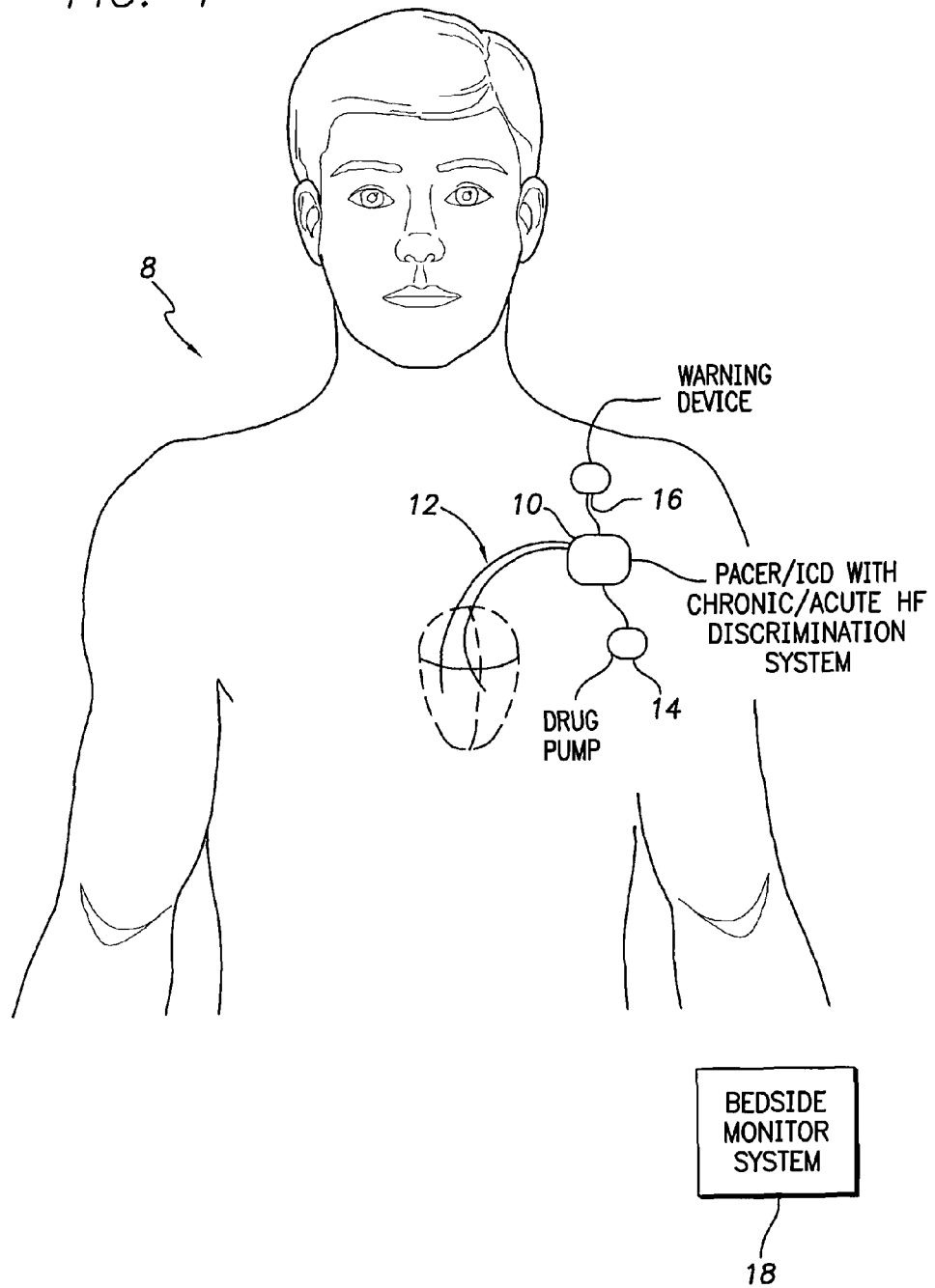
FIG. 1 illustrates an implantable medical system having a pacemaker or ICD capable of discriminating between acute and chronic heart failure, evaluating its severity and delivering therapy or warning signals in response thereto.
Figure 6:
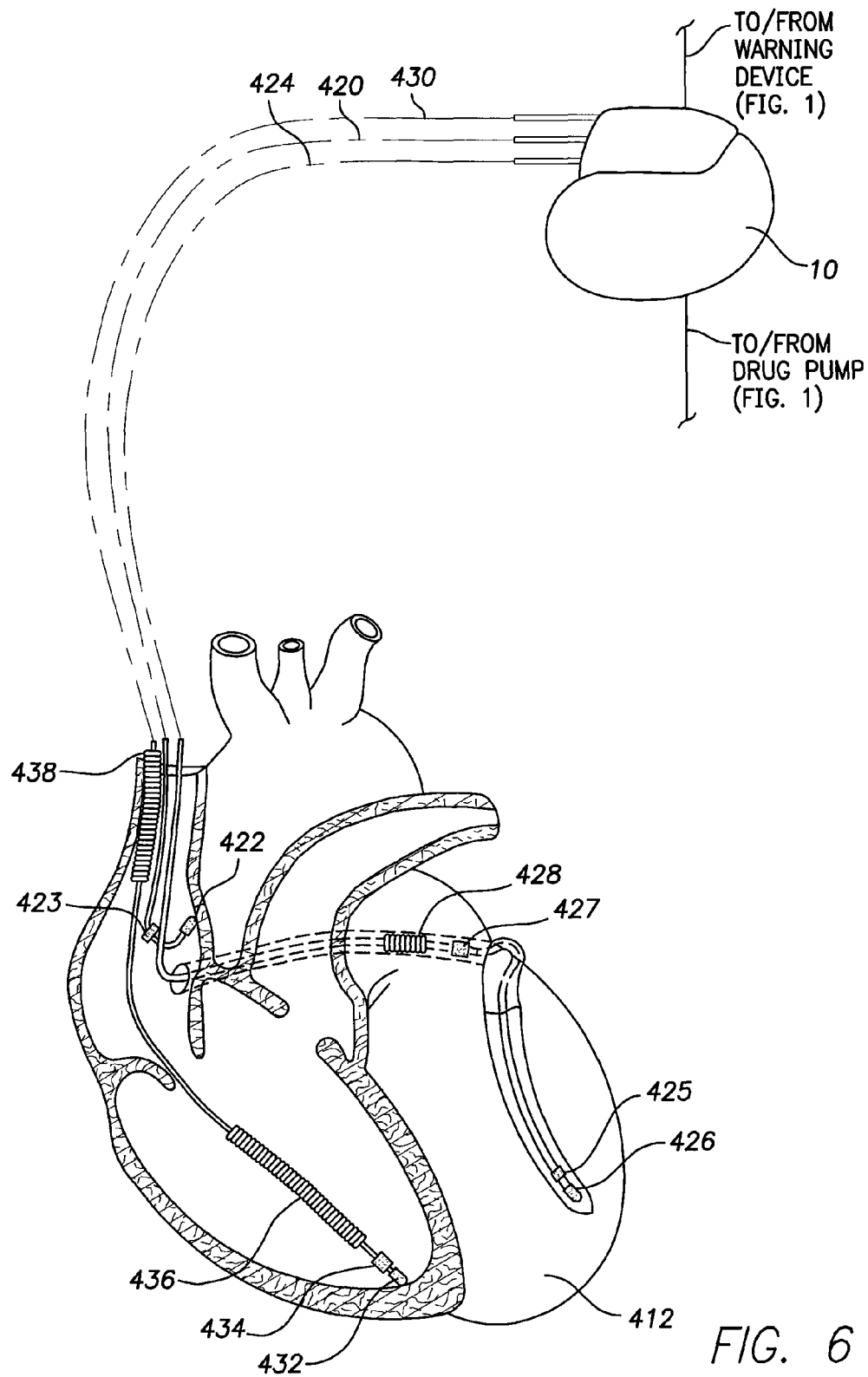
FIG. 6 is a simplified, partly cutaway view, illustrating the pacer/ICD of FIG. 1 along with at full set of leads implanted into the heart of the patient.

FIG. 1 illustrates an implantable medical system 8 capable of discriminating between acute and chronic heart failure, evaluating its severity and delivering therapy or warning signals in response thereto, as well as performing a wide range of other functions. Medical system 8 includes a pacer/ICD 10 or other cardiac stimulation device equipped with internal components for discriminating between acute and chronic heart failure via a comparison of relatively short-term changes in IEGM morphology and transthoracic impedance. The pacer/ICD also controls the delivery of therapy in response thereto. More specifically, the pacer/ICD senses electrical cardiac signals using cardiac pacing/sensing leads 12 implanted within the heart of the patient (shown stylistically in phantom lines) from which an IEGM is derived. In FIG. 1, only a two leads are shown. A more complete set of leads is shown in FIG. 6. The pacer/ICD also delivers impedance detection pulses using the leads, which are conducted back to the housing of the device, from which transthoracic impedance is determined. The pacer/ICD detects and discriminates between acute and chronic heart failure based on a comparison of changes, if any, in certain morphological features of the IEGM signals and changes, if any, in transthoracic impedance, using techniques to be described more fully below. The pacer/ICD also evaluates the severity of heart failure.

If heart failure is detected, appropriate therapy is automatically delivered by the implantable system under the control of the pacer/ICD. For example, CRT therapy may be delivered to the heart of the patient using the ventricular leads in an effort to improve cardiac function. Control parameters for CRT therapy are automatically adjusted based on the severity of the heart failure. Additionally, or in the alternative, the implantable system may be equipped with a drug pump 14 capable of the delivering drug therapy in an attempt to address heart failure. Drug dosages provided by an implantable drug pump may be titrated based on the severity of heart failure. Implantable drug pumps are discussed in U.S. Pat. No. 5,328,460 to Lord, et al., entitled "Implantable Medication Infusion Pump Including Self-Contained Acoustic Fault Detection Apparatus".

Warning signals are generated using either an internal warning device 16 or an external bedside monitor 18 so as to notify the patient of the onset of heart failure or to advise the patient of any significant progression thereof. Internal warning device 16 may be a vibrating device or a "tickle" voltage device that, in either case, provides perceptible stimulation to the patient to alert the patient of any significant progression of heart failure so that the patient may immediately consult a physician. Tickle warning devices are also described in the Lord et al. patent. The bedside monitor provides audible or visual alarm signals to alert the patient as well as textual or graphic displays. In addition, once heart failure has been detected, diagnostic information is stored within the pacer/ICD for subsequent transmission to an external programmer (not shown in FIG. 1) for review by a physician or other medial professional. The physician may then prescribe any other appropriate therapies to address the heart failure. The physician may also adjust the operation of the pacer/ICD to activate, deactivate or otherwise control any therapies that are automatically applied. In addition, the bedside monitor may be directly networked with a centralized computing system, such as the HouseCall™ system of St. Jude Medical, for immediately notifying the physician of a significant increase in heart failure severity. Networking techniques for use with implantable medical systems are set forth, for example, in U.S. Pat. No. 6,249,705 to Snell, entitled "Distributed Network System for Use with Implantable Medical Devices". If severe heart failure is detected, urgent warnings are provided both to the patient and to the appropriate medical personnel so that immediate action can be taken.

Hence, FIG. 1 provides an overview of an implantable system for discriminating between acute and chronic heart failure, evaluating its severity and delivering therapy or warning signals in response thereto. Individual systems may be implemented that do not necessarily perform all of these functions. For example, systems provided in accordance with the invention need not include all the components shown in FIG. 1. In many cases, for example, the system will include only the pacer/ICD and its leads, with heart failure therapy provided exclusively in the form of CRT. Drug pumps and implantable warning devices are not necessarily implanted. Other implementations may employ an external monitor for generating warning signals but no internal warning device. These are just a few exemplary embodiments. No attempt is made herein to describe all possible combinations of components that may be provided in accordance with the general principles of the invention.

In addition, although internal signal transmission lines provided are illustrated in FIG. 1 for interconnecting the various implanted components, wireless signal transmission may alternatively be employed. In addition, the particular locations of the implanted components shown in FIG. 1 are merely illustrative and may not necessarily correspond to actual implant locations.

Overview of the Heart Failure Discrimination Technique

Figure 2:
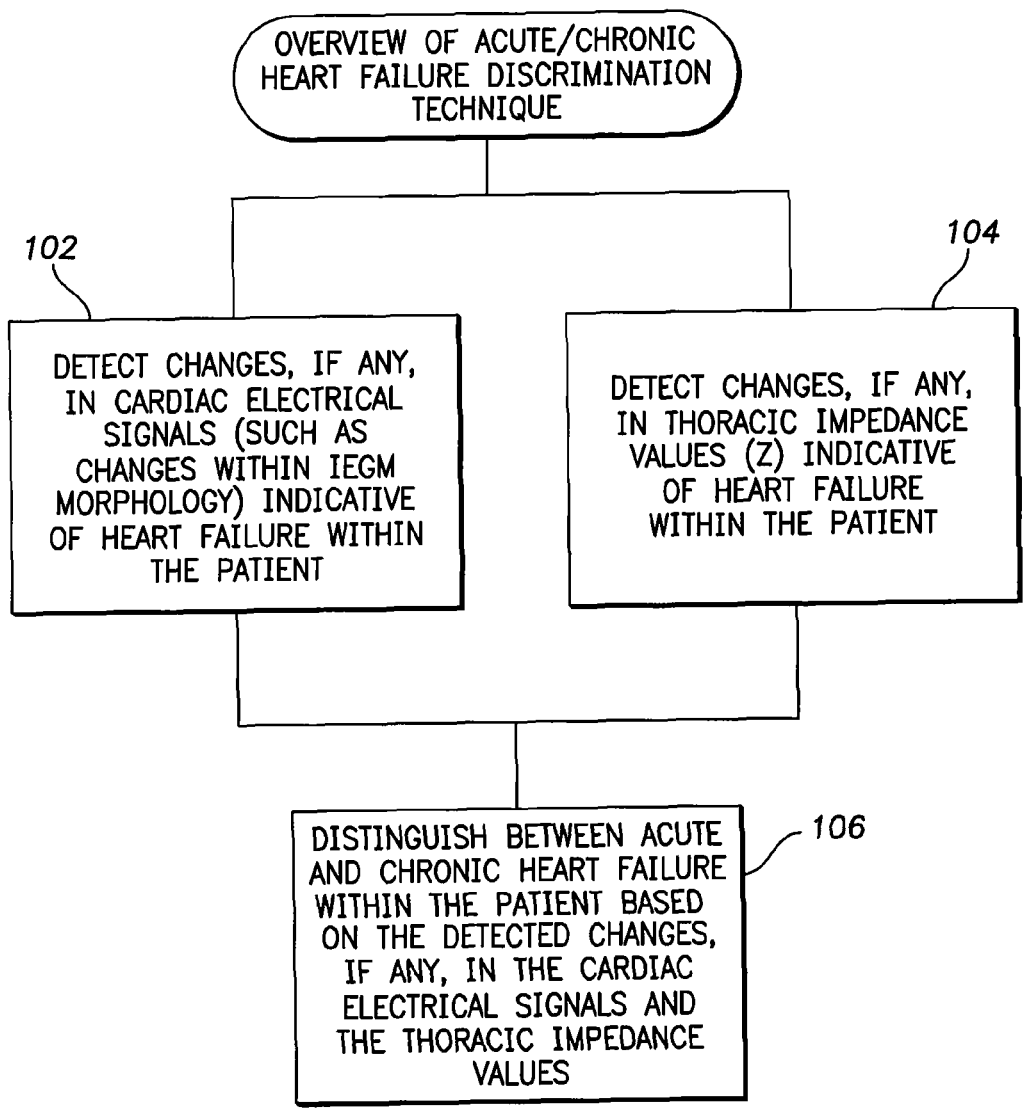
FIG. 2 provides an overview of the technique for discriminating acute and chronic heart failure performed by the system of FIG. 1.

FIG. 2 summarizes the heart failure discrimination technique that may be performed using the system of FIG. 1. Beginning with step 102, the pacer/ICD detects changes, if any, in cardiac electrical signals indicative of heart failure within the patient. Such changes may include decreases in ventricular PDI, peak-to-peak QRS-complex amplitudes, and Dmax, as derived from a ventricular IEGM. Techniques for detecting IEGMs and extracting certain morphological features therefrom are set forth in, for example, U.S. Pat. No. 7,069,069 to Fishler, et al., entitled "Implantable Cardiac Device for and Method of Monitoring Progression or Regression of Heart Disease by Quantifying Morphological Features." Contemporaneously, at step 104, the pacer/ICD detect changes, if any, in transthoracic impedance values (Z) indicative of heart failure within the patient, particularly a decrease in impedance measured from a ventricular tip electrode to the housing of the device itself. Techniques for detecting impedance are set forth in, e.g., U.S. Pat. No. 5,817,135 to Cooper, et al. entitled, "Rate-Responsive Pacemaker with Noise-Rejecting Minute Volume Determination" and U.S. Pat. No. 5,861,008 to Obel, et al., entitled "Heart Stimulating Device with Stimulation Energy Responsive to Detected Noise".

At step 106, the pacer/ICD distinguishes between acute and chronic heart failure within the patient based on the detected changes, if any, in the cardiac electrical signals and in the transthoracic impedance values. In one example, to be described in more detail below, the pacer/ICD examines relatively recent changes, if any, in IEGM signal morphology and in transthoracic impedance. As already noted, IEGM morphology does not change significantly over the short term within patients suffering from chronic heart failure. This is appears to be true because the most significant changes in heart wall thickness and contractility (which effect IEGM morphology) caused by the initial onset of heart failure have already occurred during a prior acute phase of heart failure. Within the chronic phase, relatively smaller changes, if any, in heart wall thickness and contractility occur. In contrast, transthoracic impedance does not change significantly over the short term in patients suffering from acute heart failure. This appears to be true because acute heart failure has not yet had a chance to trigger an increase in pulmonary congestives sufficient to cause a significant reduction in impedance. Hence, a significant change over the short term in IEGM parameters indicative of heart failure along with relatively minimal change in transthoracic impedance indicates acute heart failure. Conversely, a significant decrease over the short term in transthoracic impedance along with relatively minimal change in the IEGM parameters instead indicates chronic heart failure. If both IEGM morphology and transthoracic impedance change significantly over the short term, such is an indication a severe, life threatening heart failure.

Figure 3:
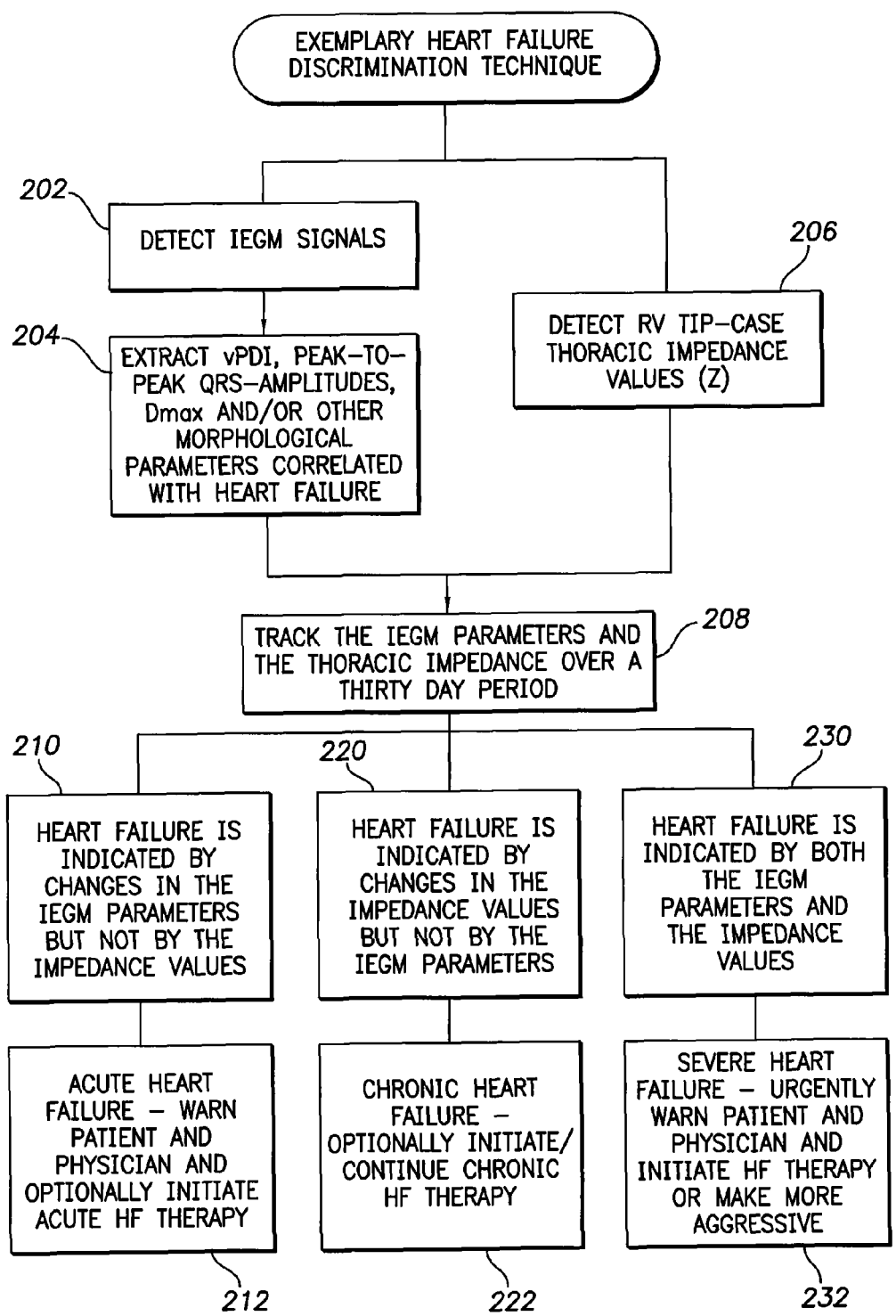
FIG. 3 illustrates an example of the discrimination technique of FIG. 2 wherein the device distinguishes between acute, chronic and severe heart failure.

Turning now to FIG. 3, an illustrative embodiment will be described wherein the pacer/ICD tracks IEGM signal morphology and transthoracic impedance over a thirty-day period. At step 202, the pacer/ICD detects ventricular IEGM signals. At step 204, the pacer/ICD extracts ventricular PDI, peak-to-peak QRS-complex amplitudes, Dmax or other morphological parameters correlated with heart failure. As noted, PDI is derived from an integral of certain portions of the IEGM. (See U.S. Pat. No. 4,759,366, to Callaghan.) The peak-to-peak amplitude of the QRS-complex is the total voltage swing from the maximum positive voltage of the QRS-complex to the maximum negative voltage of the same QRS-complex. Dmax is the maximum positive slope of the QRS-complex (also referred to as Δmax). Other parameters may instead be used, so long as there is an adequate correlation with heart failure. (Examples of some other parameters are set forth in the Fishler, et al. patent, cited above. The various parameters are derived from the IEGM using otherwise conventional signal processing techniques. Preferably, the parameters are derived only from IEGMs detected while the patient is asleep (or otherwise not active) and only following the acute phase of lead implant (during which time tissue growth around the electrodes may affect the voltage signals used to derive the IEGM.)

Figure 4:
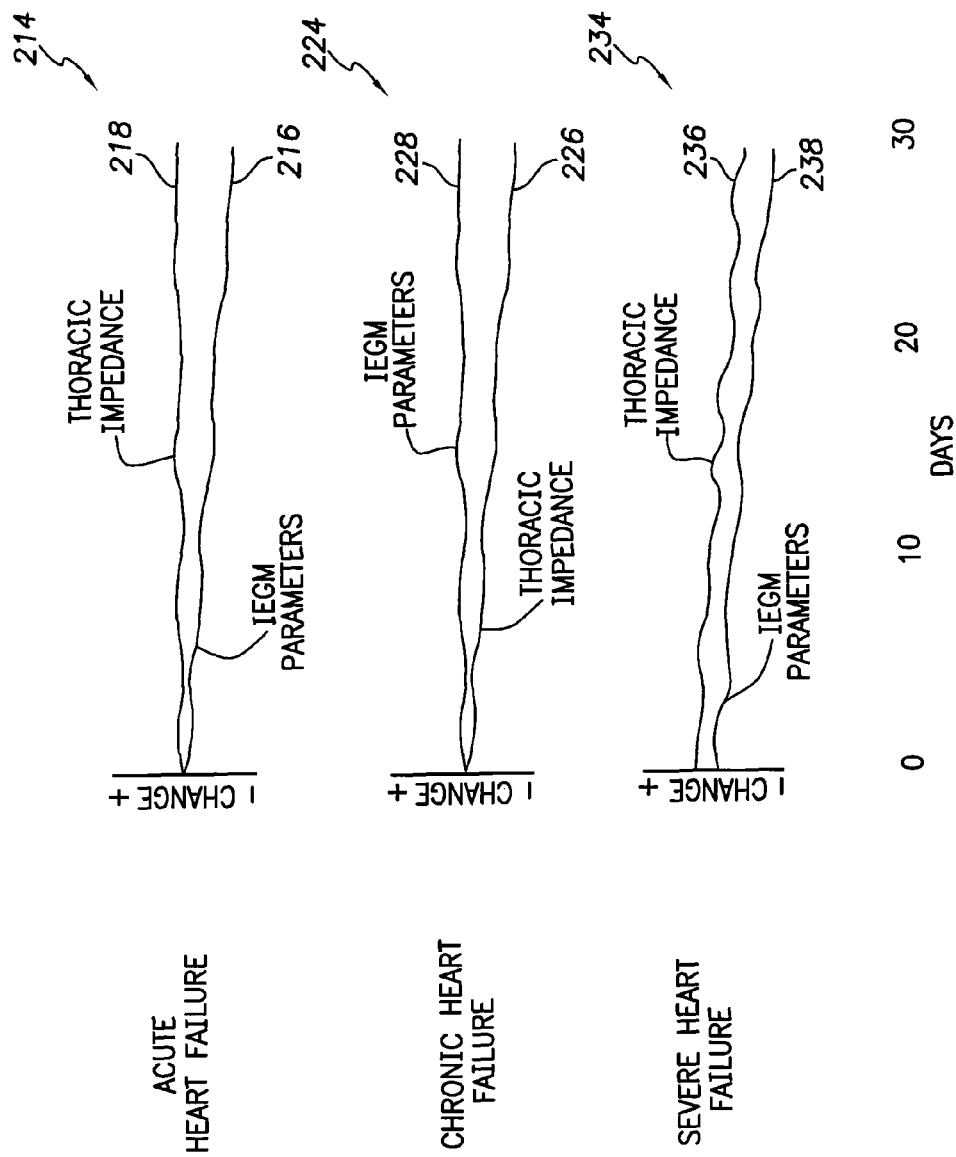
FIG. 4 provides stylized diagrams illustrating changes in IEGM morphology and transthoracic impedance parameters evaluated by the technique of FIG. 3 for patients with acute, chronic and severe heart failure.

Contemporaneously, at step 206, the pacer detects RV tip-case or RV ring-case transthoracic impedance values (Z) by selectively delivering impedance detection pulses. (The use of RV electrodes rather than LV electrodes provides an impedance signals that correlates somewhat more strongly with lung congestion.) At step 208, the pacer/ICD tracks the IEGM parameters and the transthoracic impedance (Z) over a thirty-day period, i.e. over the most recent thirty days. If heart failure is indicated by changes in the IEGM parameters but not by the impedance values, step 210, then the heart failure is likely within the acute phase and, at step 212, the patient and physician are warned accordingly. This scenario is illustrated in FIG. 4 by way of graph 214, which shows a gradual decline in IEGM parameters 216 indicative of heart failure but little or no net change in transthoracic impedance values 218 over a thirty-day period. Since the heart failure is not yet necessarily life threatening, the warnings issued at step 212 of FIG. 3 need not be as urgent as warnings of severe heart failure. If the pacer/ICD is equipped to deliver any therapy specific to acute heart failure, then the pacer/ICD can be programmed to automatically initiate such therapy. However, in many cases, the physician will prefer to perform an independent diagnosis of heart failure before such therapies are initiated and so the pacer/ICD will not be programmed to initiate such therapies on its own. In any case, diagnostic data is preferably stored for physician review. The diagnostic data may also be relayed to the physician via the bedside monitor (18 of FIG. 1) and any communication network connected thereto.

In contrast, if heart failure is indicated by changes in the impedance values but not by changes in the IEGM parameters, step 220, then the heart failure is likely within the chronic phase and, at step 222, the patient and physician are warned accordingly. This scenario is illustrated in FIG. 4 by way of graph 224, which shows a gradual decline in transthoracic impedance 226 with little or no net change in the IEGM parameters 228 that are indicative of heart failure, over the same thirty-day period. Note that, with chronic heart failure, the physician will likely already have diagnosed the heart failure from previous examinations of the patient. Accordingly, perhaps the more important diagnostic information provided here is the indication of the onset of possible pulmonary edema. Accordingly, the warnings delivered to the patient and physician preferably also indicates the presence of lung congestives indicative of the onset of possible pulmonary edema. If the pacer/ICD is equipped to deliver any therapy specific to chronic heart failure and/or pulmonary edema, then the pacer/ICD can be programmed to automatically initiate such therapy. However, in many cases, the physician will prefer to perform an independent diagnosis of heart failure and/or pulmonary edema before such therapies are initiated and so the pacer/ICD will not be programmed to initiate such therapies on its own. In any case, diagnostic data is preferably stored for physician review and relayed to the physician.

If heart failure is indicated both by changes in the impedance values and by changes in the IEGM parameters, step 230, then the heart failure is deemed to be severe and, at step 232, urgent warnings are delivered to the patient and physician. This scenario is illustrated in FIG. 4 by way of graph 234, which shows both a gradual decline in transthoracic impedance 236 and a gradual decline the IEGM parameters 238 that are indicative of heart failure, again over the same thirty-day period. The warnings delivered to the patient and physician preferably warn of both severe heart failure and possible pulmonary edema, both of which are potentially life threatening. If the pacer/ICD is equipped to deliver any heart failure therapy and/or pulmonary edema therapy, then the pacer/ICD preferably automatically immediately initiates such therapy. If heart failure therapy is already being applied, the device preferably increases the aggressiveness of any such therapy. Also, diagnostic data is preferably relayed immediately to the physician.

Thus, FIGS. 3-4 illustrate an exemplary technique for providing an indication of heart failure and/or pulmonary edema and for discriminating between acute and chronic heart failure. It should be understood that the technique does not conclusively detect either heart failure and/or pulmonary edema and a final diagnosis is preferably left to the physician. However, the technique provides an indication of such conditions at least sufficient to warrant warning the patient and the physician. Various factors may affect the accuracy of the detection technique. For example, medications may affect the IEGM parameters used in the detection/discrimination procedure. Structural changes in the heart due to myocardial ischemia may affect IEGM parameters as well. In addition, lung congestion may develop that is not the result of heart failure but arises from other conditions.

The specificity with which the pacer/ICD detects heart failure and/or pulmonary edema can be enhanced by additionally employing other, separate detection techniques. See, for example, heart failure detection/evaluation techniques set forth in: U.S. Pat. No. 6,922,587, entitled "System and Method for Tracking Progression of Left Ventricular Dysfunction using Implantable Cardiac Stimulation Device"; U.S. Pat. No. 6,942,622, entitled "Method for Monitoring Autonomic Tone"; U.S. Pat. No. 6,748,261, entitled "Implantable Cardiac Stimulation Device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease And Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; U.S. Pat. No. 6,527,729, entitled "Method for Monitoring Patient Using Acoustic Sensor", U.S. Pat. No. 6,512,953, entitled "System and Method For Automatically Verifying Capture during Multi-Chamber Stimulation" and U.S. Pat. No. 6,480,733, entitled "Method for Monitoring Heart Failure", each assigned to Pacesetter, Inc. See, also, U.S. patent application Ser. No. 11/014,276, filed Dec. 15, 2004, of Bornzin et al., entitled "System and Method for Predicting a Heart Condition Based on Impedance Values using an Implantable Medical Device", U.S. patent application Ser. No. 10/792,305, filed Mar. 2, 2004, entitled "System and Method for Diagnosing and Tracking Congestive Heart Failure based on the Periodicity of Cheyne-Stokes Respiration using an Implantable Medical Device", and U.S. patent application Ser. No. 11/397,066, entitled "QT-Based System and Method for Detecting and Distinguishing Dilated Cardiomyopathy and Heart Failure using an Implantable Medical Device", also assigned to Pacesetter, Inc. Pulmonary edema detection techniques are set forth in the various patents/patent applications cited above in the Background section.

Figure 5:
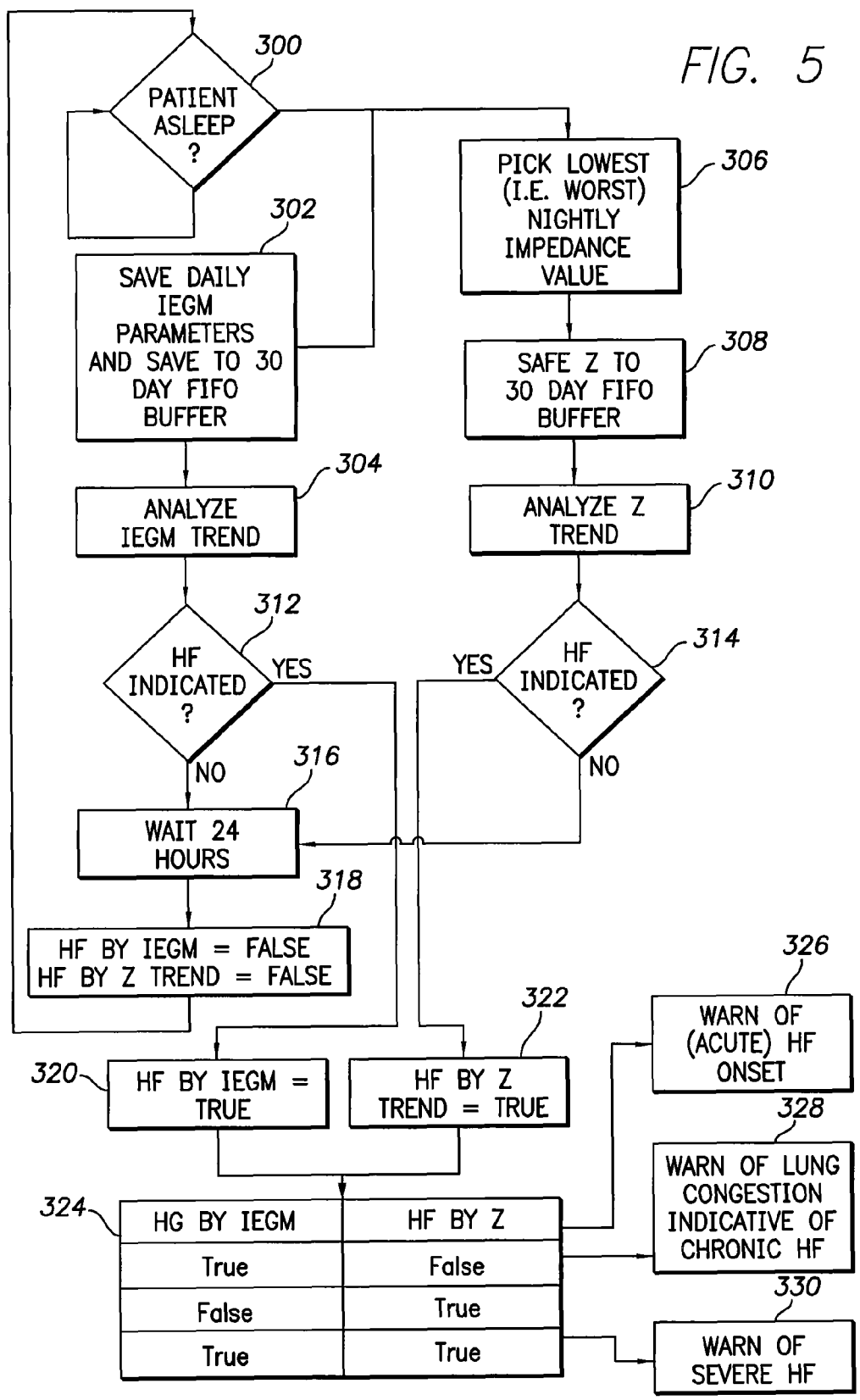
FIG. 5 illustrates a more specific example of the discrimination technique of FIG. 2 wherein the device analyzes short term IEGM and transthoracic impedance data stored in 30-day first in-first out (FIFO) buffers.

FIG. 5 illustrates a more specific example, wherein a 30-day FIFO buffer is used to store the pertinent IEGM and transthoracic impedance data so as to reduce the memory and processor burdens on the implanted device. Beginning at step 300, the pacer/ICD determines whether the patient is asleep (or otherwise not active) using, for example, an activity variance sensor. See U.S. Pat. No. 5,476,483 to Bornzin et al., entitled "System and Method for Modulating the Base Rate during Sleep for a Rate-responsive Cardiac Pacemaker". Implantable activity sensors are also described in, for example, U.S. Pat. No. 6,002,963 to Mouchawar, et al., entitled "Multi-Axial-Accelerometer-Based Sensor for an Implantable Medical Device and Method of Measuring Motion Measurements Therefor". Examples of other sleep detection techniques are set forth in: U.S. Pat. No. 6,128,534 to Park et al., entitled "Implantable Cardiac Stimulation Device and Method for Varying Pacing Parameters to Mimic Circadian Cycles" and in patent application Ser. No. 10/339,989, to Koh et al., entitled "System and Method for Detecting Circadian States Using an Implantable Medical Device", filed Jan. 10, 2003.

If the activity variance falls below a threshold indicative of sleep, the pacer/ICD initiates a procedure to evaluate heart failure. At step 302, the pacer/ICD extracts the IEGM parameters (such as vPDI, peak-to-peak amplitudes, Dmax) indicative of heart failure from the IEGM and stores the parameters in a 30-day FIFO buffer. Preferably, the parameters are averaged over the course of the sleep period (or over a significant portion thereof) and only a single value representative of each pertinent parameter is actually stored in the FIFO buffer per day, i.e. an average vPDI, an average peak-to-peak amplitude and an average Dmax. Next at step 304, the pacer/ICD analyzes the stored IEGM data in the FIFO buffer to detect trends, if any, in the data. Otherwise conventional numerical processing techniques can be used to detect a significant change, if any, in the parameters, such as linear regression analysis. Contemporaneously, at step 306, the pacer/ICD also detects transthoracic impedance values over the course of the sleep period. However, rather than averaging the impedance values, the pacer/ICD preferably selects the lowest (i.e. worst) impedance value detected over the course of the evening. At step 308, the selected Z value is stored in a 30-day FIFO buffer and the data in the buffer is analyzed to detect any significant trend, again using otherwise conventional numerical processing techniques.

At steps 312 and 314, the pacer/ICD determines whether heart failure is indicated by either the IEGM or Z data. If neither indicates heart failure, then the pacer/ICD waits 24 hours, at step 316, before repeating the procedure. The pacer/ICD also sets two flags to FALSE: an "HF by IEGM" flag and an "HF by Z trend" flag to indicate that heart failure is not indicated, at step 318. However, if either the IEGM or the impedance analysis indicates heart failure, then processing proceeds to steps 320 and/or 322. At step 320, the "HF by IEGM" flag is set to TRUE to indicate possible heart failure via IEGM analysis. At step 322, the "HF by Z trend" flag is set to TRUE to indicate possible heart failure via impedance analysis. Processing then proceeds to step 324 wherein the pacer/ICD examines a stored truth table to determine what action is to be taken. If "HF by IEGM" flag is set to TRUE but "HF by Z trend" is FALSE then step 326 is performed wherein the pacer/ICD warns of the onset of heart failure, i.e. a warning of acute HF is issued. If "HF by IEGM" flag is set to FALSE but "HF by Z trend" is TRUE, then step 328 is instead performed wherein the pacer/ICD warns of lung congestion indicative of chronic heart failure. If both "HF by IEGM" flag and "HF by Z trend" is TRUE, then step 330 is instead performed wherein the pacer/ICD warns of severe heart failure. As already explained, therapy may additionally be initiated, depending upon the particular diagnosis.

What have been described are various techniques for detecting and discriminating heart failure and for delivering appropriate warning/therapy. For the sake of completeness, a detailed description of an exemplary pacer/ICD for controlling these functions will now be provided. However, principles of invention may be implemented within other pacer/ICD implementations or within other devices.

Exemplary Pacer/ICD

FIG. 6 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of detecting and discriminating heart failure, evaluating its severity, and controlling the delivery of therapy and warnings in response thereto. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a RV electrode 432, a RV ring electrode 434, a RV coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least an LV tip electrode 426 and an LV ring electrode 425. Left atrial pacing therapy using at least a left atrial ring electrode 427 and shocking therapy using at least a left atrial coil electrode 428. With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 7:
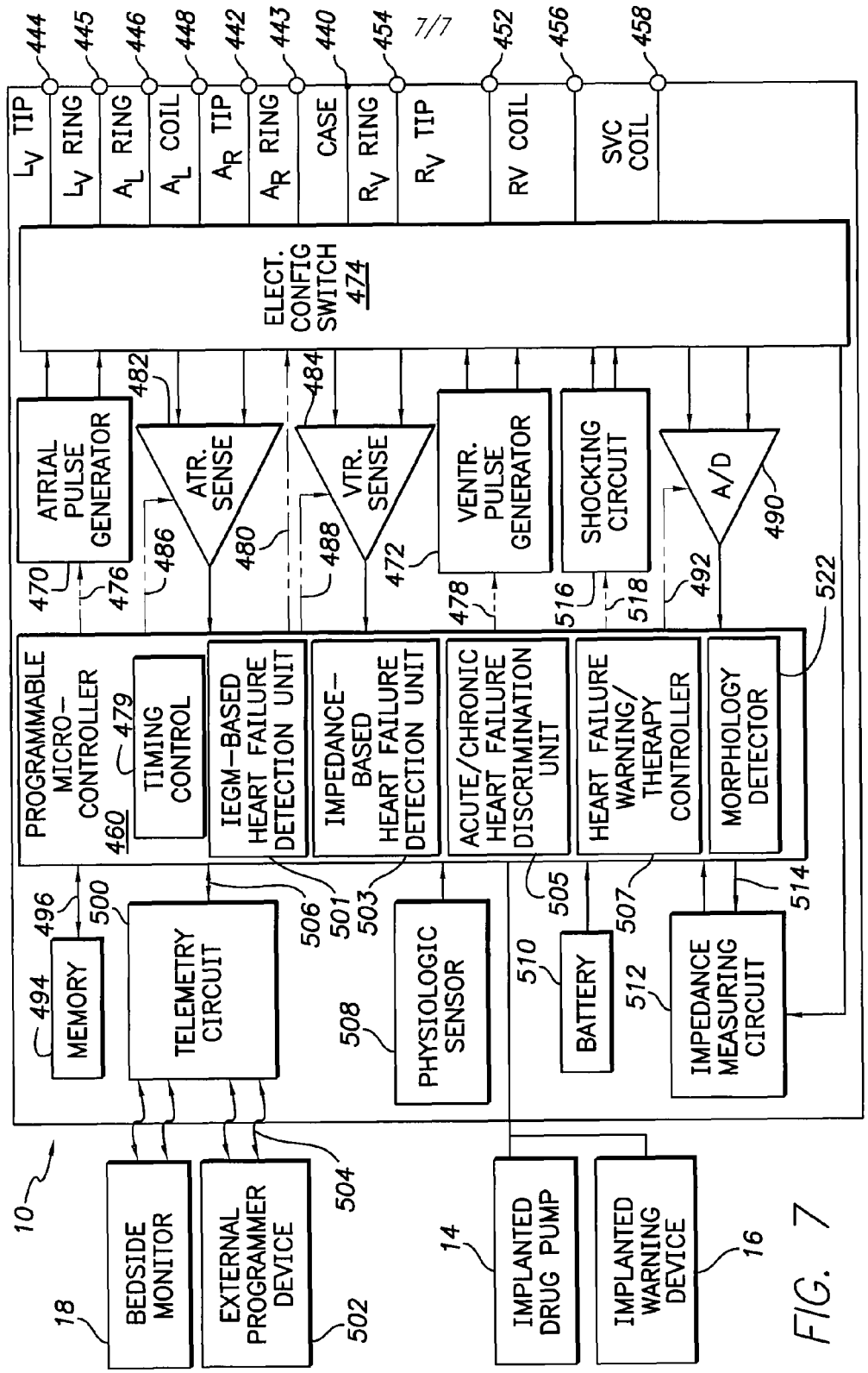
FIG. 7 is a functional block diagram of the pacer/ICD of FIG. 6, illustrating basic circuit elements that provide cardioversion, defibrillation and/or pacing stimulation in the heart and particularly illustrating components for discriminating between acute and chronic heart failure, evaluating its severity and delivering therapy or warning signals in response thereto.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned heart failure discrimination and therapy.

The housing 440 for pacer/ICD 10, shown schematically in FIG. 7, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 445, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left ventricular ring terminal (LV RING) 445, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively. Additional terminals, not shown, may be provided for connecting to an implanted drug pump and an implanted warning device.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 7, an atrial pulse generator 470 and a ventricular/impedance pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fibwaves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks), collectively referred to as "tiered therapy"). Morphology detection is performed by morphology detector 522.

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502 and/or a bedside monitor 18. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 (and/or a bedside monitor 18) through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes at least one battery 510 of other power source, which provides operating power to all of the circuits shown in FIG. 7. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 7, pacer/ICD 10 includes an impedance measuring circuit 512 that is enabled by the microcontroller 460 via a control signal 514. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring transthoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit is also equipped to measure transthoracic impedance.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Microcontroller 460 also includes various components directed to the evaluation of heart failure including an IEGM-based heart failure detection unit 501 operative to detect heart failure within the patient based on changes in IEGM signals and an impedance-based heart failure detection unit 503 operative to detect heart failure within the patient based on changes in thoracic impedance. A acute/chronic heart failure discrimination unit 505 is also provided that is operative to distinguish between acute and chronic heart failure within the patient based on the output signals provided by the IEGM-based heart failure detection unit and the impedance-based heart failure detection unit, in accordance with techniques already described. A heart failure therapy/warning controller 507 controls delivery of therapy and/or warning signals in response to the evaluation heart failure, again in accordance with techniques already described. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller.

Although described with respect to exemplary systems and techniques, principles of the invention may be exploiting using other implantable systems or in accordance with other techniques. Indeed, general principles invention may be exploited with systems not incorporating pacemakers or ICDs but instead incorporating other implantable medical devices. As can be appreciated, a wide variety of specific implementations may be developed consistent with the principles of the invention and no attempt is made herein to describe or enumerate all such possible implementations. Thus, while the invention has been described with reference to particular embodiments, modifications can be made thereto without departing from the scope of the invention. Note also that the term "including" as used herein is intended to be inclusive, i.e. "including but not limited to".

What is claimed is:

1. A method for evaluating heart failure within a patient using an implantable medical device, the method comprising:
    detecting changes, if any, in cardiac electrical signals indicative of heart failure within the patient;
    detecting changes, if any, in transthoracic impedance values indicative of heart failure within the patient; and
    distinguishing between acute and chronic heart failure, if occurring within the patient, based on detected changes in the cardiac electrical signals and the transthoracic impedance values, wherein acute heart failure is relatively short term as compared to chronic heart failure;
    wherein distinguishing between acute and chronic heart failure within the patient includes (a) generating an indication of acute heart failure if the cardiac signals indicate the presence of heart failure whereas the impedance values exhibit little or no net change in value and (b) generating an indication of chronic heart failure if the impedance values indicate the presence of heart failure whereas the cardiac signals exhibit little or no net change in value.

2. The method of claim 1 wherein the cardiac electrical signals are intracardiac electrogram (IEGM) signals.

3. The method of claim 2 wherein detecting changes, if any, in the IEGM signals includes detecting a decrease in one or more of paced depolarization integrals (PDI) derived from the IEGM, peak-to-peak amplitudes of QRS-complexes within the IEGM, and a maximum slope (Dmax) of the QRS-complex.

4. The method of claim 2 wherein detecting changes, if any, in the IEGM signals includes:
    extracting parameters indicative of possible heart failure from the IEGM;
    determining a daily value representative of the extracted parameters;
    storing the daily values within a multi-day IEGM buffer; and
    examining the values of the multi-day IEGM buffer to detect any trends in the daily values indicative of heart failure.

5. The method of claim 4 wherein the multi-day IEGM buffer covers at least 30 days.

6. The method of claim 2 wherein extracting parameters indicative of possible heart failure from the IEGM is performed only while the patient is not active.

7. The method of claim 1 wherein detecting changes, if any, in transthoracic impedance values includes detecting decreases in transthoracic impedance values indicative of pulmonary edema secondary to heart failure.

8. The method of claim 7 wherein detecting changes, if any, in the transthoracic impedance values includes:
    detecting transthoracic impedance values while the patient is not active;
    identifying the lowest impedance value on a daily basis;
    storing the lowest impedance value within a multi-day impedance buffer; and
    examining the values of the multi-day impedance buffer to detect any trends in the daily values indicative of pulmonary edema secondary to heart failure.

9. The method of claim 8 wherein the multi-day impedance buffer covers at least 30 days.

10. The method of claim 1 further including:
    evaluating the severity of heart failure within the patient based on the impedance values and the cardiac signals.

11. The method of claim 10 further including issuing a warning indicative of the severity of heart failure.

12. The method of claim 1 further including issuing a signal indicative of the type of heart failure, the signal indicating either acute or chronic heart failure.

13. The method of claim 1 further including the step of controlling the storage of diagnostic information indicative of the type of heart failure, the information indicating either acute or chronic heart failure.

14. A system for evaluating heart failure within a patient for use with an implantable medical device, comprising:
    an IEGM-based heart failure detection unit adapted to detect heart failure within the patient based on changes, if any, in IEGM signals;
    an impedance-based heart failure detection unit adapted to detect heart failure within the patient based on changes, if any, in thoracic impedance; and
    a heart failure discrimination unit adapted to distinguish between acute and chronic heart failure within the patient based on output signals provided by the IEGM-based heart failure detection unit and the impedance-based heart failure detection unit, wherein acute heart failure is relatively short term as compared to chronic heart failure; wherein the heart failure discrimination unit is adapted to (a) generate an indication of acute heart failure if the cardiac signals indicate the presence of heart failure whereas the impedance values exhibit little or no net change in value, and to (b) generate an indication of chronic heart failure if the impedance values indicate the presence of heart failure whereas the cardiac signals exhibit little or no net change in value.

15. The system of claim 14 further including:
a warning controller adapted to generate an indication of the severity of heart failure based on an evaluation of the output signals provided by the IEGM-based heart failure detection unit and the impedance-based heart failure detection unit.

16. A system for evaluating heart failure within a patient for use with an implantable medical device, comprising:
means for detecting changes, if any, in cardiac electrical signals indicative of heart failure within the patient;
means for detecting changes, if any, in transthoracic impedance values indicative of heart failure within the patient; and
means for distinguishing between acute and chronic heart failure within the patient based on detected changes in the cardiac electrical signals and the transthoracic impedance values, wherein acute heart failure is relatively short term as compared to chronic heart failure; wherein the means for distinguishing between acute and chronic heart failure within the patient includes (a) means for generating an indication of acute heart failure if the cardiac signals indicate the presence of heart failure whereas the impedance values exhibit little or no net change in value and (b) means for generating an indication of chronic heart failure if the impedance values indicate the presence of heart failure whereas the cardiac signals exhibit little or no net change in value.

17. A method for evaluating heart failure within a patient using an implantable medical device, the method comprising:
detecting changes, if any, in cardiac electrical signals indicative of heart failure within the patient;
detecting changes, if any, in transthoracic impedance values indicative of heart failure within the patient;
generating an indication of acute heart failure if the cardiac signals indicate the presence of heart failure whereas the impedance values exhibit little or no net change in value;
generating an indication of chronic heart failure if the impedance values indicate the presence of heart failure whereas the cardiac signals exhibit little or no net change in value, wherein acute heart failure is relatively short term as compared to chronic heart failure; and
evaluating the severity of heart failure within the patient based on the impedance values and the cardiac signals.

* * * * *